United States Patent
Cajan et al.

(10) Patent No.: US 9,592,191 B2
(45) Date of Patent: Mar. 14, 2017

(54) HAIR TREATMENT METHOD

(71) Applicant: KAO GERMANY GMBH, Darmstadt (DE)

(72) Inventors: Christine Cajan, Bad-Ems (DE); Masayoshi Ehara, Tokyo (JP); Sabine Schmid, Ginsheim-Gustavsburg (DE)

(73) Assignee: KAO GERMANY GMBH, Darmstadt (DE)

( * ) Notice: Subject to any disclaimer, the term of this patent is extended or adjusted under 35 U.S.C. 154(b) by 0 days.

(21) Appl. No.: 14/376,294

(22) PCT Filed: Feb. 2, 2013

(86) PCT No.: PCT/EP2013/053295
§ 371 (c)(1),
(2) Date: Aug. 1, 2014

(87) PCT Pub. No.: WO2013/124277
PCT Pub. Date: Aug. 29, 2013

(65) Prior Publication Data
US 2015/0007849 A1    Jan. 8, 2015

(30) Foreign Application Priority Data
Feb. 21, 2012 (EP) .................................... 12156367

(51) Int. Cl.
*A61Q 5/06* (2006.01)
*A61K 8/86* (2006.01)
*A45D 7/04* (2006.01)
*A45D 24/02* (2006.01)
*A46B 15/00* (2006.01)
*A45D 7/00* (2006.01)

(52) U.S. Cl.
CPC .................. *A61K 8/86* (2013.01); *A45D 7/04* (2013.01); *A45D 24/02* (2013.01); *A46B 15/0091* (2013.01); *A61Q 5/06* (2013.01); *A45D 2007/002* (2013.01); *A61K 2800/10* (2013.01); *A61K 2800/31* (2013.01)

(58) Field of Classification Search
None
See application file for complete search history.

(56) References Cited

U.S. PATENT DOCUMENTS

| | | | |
|---|---|---|---|
| 2005/0123488 A1* | 6/2005 | Brautigam et al. | 424/47 |
| 2007/0199574 A1* | 8/2007 | Ragosta et al. | 132/238 |
| 2008/0112912 A1* | 5/2008 | Springob | A61K 8/34 424/70.12 |
| 2011/0067720 A1* | 3/2011 | Ranade et al. | 132/202 |
| 2012/0031419 A1* | 2/2012 | Batt et al. | 132/203 |
| 2012/0039834 A1 | 2/2012 | Oshika et al. | |

FOREIGN PATENT DOCUMENTS

| | | |
|---|---|---|
| JP | 2011 251919 A | 12/2011 |
| WO | 2010/084993 A1 | 7/2010 |

OTHER PUBLICATIONS

International Search Report dated Jul. 3, 2014, mailed Jul. 14, 2014.

\* cited by examiner

*Primary Examiner* — Jyothsna Venkat
(74) *Attorney, Agent, or Firm* — Norris McLaughlin & Marcus PA

(57) ABSTRACT

Present invention relates to a hair treatment method for setting hair style and its restyling including a step of application of an anhydrous spray on wet hair. The present invention is a method of treating hair comprising the step of applying a substantially anhydrous composition comprising one or more polymers according to the general structure

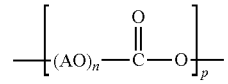

wherein A is a C2 to C6 alkylene group and n represents an average number of 5 to 1000 and p represents an average number of 5 to 100 and (n×p) units of AO may be the same or not onto wet hair.

12 Claims, No Drawings

HAIR TREATMENT METHOD

This application is a 371 application of PCT/EP2013/053295 filed Feb. 19, 2013, which claims foreign priority benefit under 35 U.S.C. §119 of European Application No. 12156367.0 filed Feb. 21, 2012, the disclosures of which are all incorporated herein by reference.

Present invention relates to a hair treatment method for setting hair style and its restyling including a step of application of an anhydrous spray on wet hair.

Hair styling includes the use of after bath products which are usually applied on wet and/or dry hair. Traditionally anhydrous aerosol sprays are always applied onto dry hair for bringing hair into its final shape and to assure long lasting hair style. Usually once styling polymer dried on the hair surface, it is not possible to restyle hair without using any additional styling product. It is usual that hair is first cleansed and subsequently treated hair with additional styling products for achieving new styles. This is because the dried polymer does not have any adhesive property. This brings about difficulties to women in their daily life.

Furthermore, when hair is styled with blow drying using a brush in the presence of an anhydrous styling spray already applied onto hair, this is rather difficult, if not impossible, because of increasing stickiness of polymer layer on hair with reduced hair humidity. The problem is that hair gets almost impossible to comb or brush through. In order to style hair with blow drying and brushing, it has always been required to use aqueous compositions such as mousses or lotions which may be applied onto hair using a pump-spray.

Inventors of the present invention have been seeking for new methods which allow effective hair styling as well as restyling and which does not require using various hair styling compositions in wet and dry state but allows hair styling using a single composition in wet and/or dry state, if necessary, when styling hair with the aid of blow drying and a brush.

Inventors of the present invention have surprisingly found out that it is possible to apply an anhydrous aerosol spray composition comprising a polyether polycarbonate polymer onto wet hair and this allows styling hair with blow-drying and brushing and also allows giving hair a new style after a while.

Styling composition comprising polyether polycarbonate polymer are known from international patent application WO 2010/084993 A1. The document does not mention application of such hair styling composition onto wet hair and also remains silent on the use of such composition while blow drying and brushing.

Synthesis of polyether polycarbonate polymers are known from the above mentioned international application and also from EP 2115032 A1.

The first object of the present invention is a method of treating hair comprising the step of applying a substantially anhydrous composition comprising one or more polymers according to the general structure

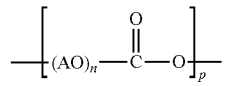

wherein A is a C2 to C6 alkylene group and n represents an average number of 5 to 1000 and p represents an average number of 5 to 100 and (n×p) units of AO may be the same or not onto wet hair.

The second object of the present invention is a method of treating hair comprising the steps of applying a substantially anhydrous composition comprising one or more polymers according to the above general structure onto wet hair and blow-drying while brushing hair.

The third object of the present invention is a kit for hair comprising a hair appliance, preferably a brush and/or a comb and a substantially anhydrous composition comprising one or more polymers according to the above general structure.

In a preferred embodiment of the present invention the polyether polycarbonate polymer according to the above general structure has an average molecular weight of 50,000 to 1,000,000. Furthermore, the (n×p) units of AO in the above general structure consist of at least two alkyleneoxy groups, preferably a combination of an ethyleneoxy group and a propyleneoxy group.

As mentioned above the polyether polycarbonate polymers are available from the two patent documents cited. The polymers disclosed in the examples of WO 2010/084993 A1 are especially suitable for the anhydrous composition of the present invention. One or more polymers are comprised in the compositions at a concentration in the range of 0.1 to 30%, preferably 0.5 to 20% more preferably 1 to 15% and most preferably 2 to 10% by weight calculated to the total composition excluding propellant in the case that the composition is confectioned in the form of an aerosol product.

With the term "substantially anhydrous", it is meant that the composition does not comprise any water added to the composition. However, water may be present as it may inevitably be introduced to the composition through the use of one or more additional components which may contain water because of being hygroscopic. The term substantially anhydrous does not cover any water inevitably be included into the compositions because of the use other substances. In any case, water content of the compositions may not exceed concentrations as low as 5%, preferably less than 4%, more preferably less than 3% and most preferably less than 1% by weight calculated to the total composition excluding propellant.

The substantially anhydrous composition is prepared by dissolving the polyether polycarbonate polymer in a solvent. Any organic solvent allowed for cosmetic application is suitable for the compositions. Preferred solvents are ethanol, propanol, isopropanol, acetone, n-pentane, isopentane and their mixtures. Most preferred is ethanol. Concentration of organic solvent is in the range of 70 to 99.9% preferably 80 to 99.5% more preferably 85 to 99% and most preferably 90 to 98% by weight calculated to the total composition excluding propellant.

According to the method of treating hair the substantially anhydrous composition is applied onto wet hair. In a preferred embodiment of the present invention the substantially anhydrous composition is applied onto wet hair which is washed with a cleansing composition and towel dried immediately before application of the substantially anhydrous composition.

The substantially anhydrous composition may be in the form of a solution and an aerosol composition. In case that the composition is in form of an aerosol composition then it comprises at least one propellant. Any propellant known to be suitable for use in hair cosmetic compositions may suitably be used for preparing the anhydrous composition. Examples of propellants include liquefied petroleum gas (LPG), dimethyl ether (DME), hydrofluorocarbon, carbon dioxide gas, nitrogen gas, and a mixture thereof. Propellants are comprised in the aerosol compositions at a concentration in the range of 1 to 95%, preferably 5 to 80%, more preferably 10 to 60% and most preferably 15 to 50% by weight calculated to the total of aerosol composition. Preferably, the excess pressure in the pressure-resistant container is regulated to 1 to 6 Bar at 25° C., so as to realize good spray performance.

The substantially anhydrous composition of the present invention may also contain additional polymers from anionic polymers. Examples of the anionic polymer include natural anionic polymers such as xanthan gum, carrageenan, sodium alginate, pectin, furcellaran, gum arabic, gum ghatti, gum karaya, gum tragacanth, agar powder, and carboxymethylcellulose; and synthetic anionic polymers such as polymers produced through polymerization of an acidic vinyl monomer or a salt thereof. As used herein, "acidic vinyl monomer" refers to a compound having in the molecule an acidic group (e.g., a carboxy group or a phosphate group) and a polymerizable vinyl group. Examples of the acidic vinyl monomer include acrylic acid, methacrylic acid, crotonic acid, vinylbenzoic acid, itaconic acid, maleic acid, and fumaric acid. Specific examples of the synthetic anionic polymer include carboxylic-acid-containing anionic polymers such as acrylic acid/ethyl aerylate/N-t-butylacrylamide copolymer (e.g., Ultrahold 8 and Ultrahold Strong, products of BASF), octylacrylamide/acrylic acid copolymer (e.g., Amphomer V-42, product of National Starch), acrylate/methacrylate/acrylic acid/methacrylic acid copolymer (e.g., Amerhold DR25, product of Union Carbide Corporation), acrylates/diacetone acrylamide copolymer (e.g., Plus Size L-9540B, product of Goo Chemical Co., Ltd.), methyl vinyl ether/alkyl maleate copolymer (e.g., Gantrez ES-225, Gantrez ES-425, and Gantrez SP-215, products of ISP), vinyl acetate/crotonic acid copolymer (e.g., Resin 28-1310, product of National Starch), vinyl acetate/crotonic acid/vinyl neodecanoate copolymer (e.g., Resin 28-2930, product of National Starch), vinyl acetate/crotonic acid/vinyl propionate copolymer (e.g., Luviset CAP, product of BASF), vinyl alcohol/itaconic acid copolymer (e.g., KM-118, product of Kuraray Co., Ltd.); and phosphate-containing anionic polymers such as homopolymers formed from a phosphate-group-containing monomer (e.g., Polyphosmer M-IOI, Polyphosmer PE-201, and Polyphosmer MH-301, product of DAP Co., Ltd.), and copolymer of a phosphate-group-containing monomer and an acrylic acid ester (e.g., Polyphosmer MHB-10, product of DAP Co., Ltd.). Of these anionic polymers, anionic set polymers are preferred, and carboxylic-acid-containing anionic set polymers are more preferred. In particular, unneutralized ones are more preferred.

The anionic polymer content of the hair cosmetic composition of the present invention is preferably in the range of 0.5 to 20 weight %, more preferably from 1 to 15 weight %, even more preferably from 1.5 to 10 weight %, calculated to the total composition excluding propellants.

The ratio by weight of the polyether polycarbonate to the anionic polymer is preferably in the range of 2:8 to 8:2, more preferably 3:7 to 7:3, most preferably 4:6 to 6:4.

For improvement of hair set retention, the substantially anhydrous composition of the present invention may contain a set polymer other than the aforementioned anionic hair styling polymers. Examples of such a set polymers include alkylacrylamide/acrylate/alkylaminoalkylacrylamide/polyethylene glycol methacrylate copolymer described in JP-A-1990-180911, alkylacrylamide/alkylaminoalkylacrylamide/polyethylene glycol methacrylate copolymer described in JP-A-1996-291206, Yukaformer R205 (product of Mitsubishi Chemical Corporation), (methacryloyloxyethylcarboxybetaine/alkyl methacrylate) copolymer (e.g., RAM Resin, product of Osaka Organic Chemical Industry Ltd.), (acrylates/lauryl acrylate/stearyl acrylate/ethyl methacrylate amine oxide) copolymer (e.g., Diaformer Z-712, product of Mitsubishi Chemical Corporation), (vinylamine/vinyl alcohol) copolymer (e.g., Diafix C-601, product of Mitsubishi Chemical Corporation), polyvinylcaprolactam (e.g., Luviskol Plus, product of BASF), alkyl acrylate copolymer (e.g., Luvimer 100P and Luvimer 3OE, products of BASF), (octylacrylamide/hydroxypropyl acrylate/butylaminoethyl methacrylate) copolymer (e.g., Amphomer SH-701, Amphomer 28-4910, Amphomer LV-71, and Amphomer LV-47, products of National Starch & Chemical), (vinylpyrrolidone/dimethylaminoethyl methacrylate) copolymer quaternized with diethyl sulfate (polyquaternium-11) (e.g., Gafquat 440, product of ISP), methyl-quaternized vinylpyrrolidone/dimethylaminopropylmethacrylamide copolymer (polyquaternium-28) (e.g., Gafquat HS-100, product of ISP), (PVP/vinylcaprolactam/DMAPA acrylate) copolymer (e.g., Aquaflex SF-40, product of ISP), (isobutylene/ethylmaleimide/hydroxyethylmaleimide) copolymer (e.g., Aquaflex FX-64, product of ISP), (vinylpyrrolidone/dimethylaminopropylmethacrylamide/methacryloylaminopropyllauryldimethylammonium chloride) copolymer (polyquaternium-55) (e.g., Styleze W-20, product of ISP), (vinylpyrrolidone/DMAPA acrylate) copolymer (e.g., Styleze CC-10, product of ISP), and (vinylpyrrolidone/vinyl acetate) copolymer (e.g., PVP/VA735 (product of ISP) and Luviskol VA64P (product of BASF)) and Plascize L2700 from Goo Chemicals. Of the aforementioned set polymers, preferred are alkylacrylamide/acrylate/alkylaminoalkylacrylamide/poly-ethylene glycol methacrylate copolymer, alkylacrylamide/alkylaminoalkylacrylamide/polyethylene glycol methacrylate copolymer, (methacryloyloxyethylcarboxybetaine/alkyl methacrylate) copolymer, (alkyl acrylate/diacetone acrylamide) copolymer neutralized with aminomethyl propanol, (octylacrylamide/hydroxypropyl acrylate/butylaminoethyl methacrylate) copolymer, acrylic acid/acrylamide/ethyl acrylate copolymer, and polyvinylcaprolactam; and more preferred are alkylacrylamide/acrylate/alkylaminoalkylacrylamide/poly-ethylene glycol methacrylate copolymer, and alkylacrylamide/alkylaminoalkylacrylamide/polyethylene glycol methacrylate copolymer. The set polymer content of the substantially anhydrous composition of the present invention is preferably 0.5 to 20%, more preferably 1 to 15%, most preferably 1.5 to 10% by weight calculated to total composition excluding propellants.

The substantially anhydrous composition of the present invention may contain, in addition to the aforementioned components, an oil component at a concentration in the range of 0.01 to 10% by weight calculated to total composition excluding propellant, so long as the oil component does not impede the effects of the present invention. Examples of the oil component include glycerides such as castor oil, cocoa oil, mink oil, avocado oil, argan oil and olive oil; waxes such as beeswax, whale wax, lanolin, and carnauba wax; higher alcohols such as cetyl alcohol, oleyl alcohol, hexadecyl alcohol, lauryl alcohol, stearyl alcohol, isostearyl alcohol, and 2-octyldodecanol; esters such as isopropyl myristate, hexyl laurate, cetyl lactate, propylene glycol monostearate, oleyl oleate, hexadecyl 2-ethylhexanoate, and octyldodecyl myristate; hydrocarbon oils such as liquid paraffin, vaseline, squalane, and hydrogenated polyisobutene,—silicone derivatives such as dimethylpolysiloxane, methylphenylpolysiloxane, polyether-modified silicone oil, epoxy-modified silicone oil, amino-modified silicone oil, and alkyl-modified silicone oil; and polypropylene glycol.

The substantially anhydrous composition of the present invention may also contain a perfume or a dye for improving its commercial value, or a preservative or an antioxidant for preventing change over time in quality of the hair cosmetic composition. Also, the substantially anhydrous composition may optionally contain, for example, a moisture controlling agent (e.g., glycerin or propylene glycol), a curing agent, an antistatic agent, a surfactant, an antifoaming agent, a dispersant, a thickener, a UV-absorbing agent, an antioxidant, a preservative, a coloring dye, a dye fixative, or a propellant.

Following examples are to illustrate the invention, but not to limit.

Throughout the examples the polyether polycarbonate polymers use are according to the disclosure of the international patent application WO 2010/084993 of Kao Corporation and designated in the same way such as Polyether polycarbonate 1 (according to Synthetic Example 1 of WO 2010/084993), Polyether polycarbonate 2 (according to Synthetic Example 2 of WO 2010/084993), etc.

EXAMPLE 1

|  | % by weight |
| --- | --- |
| Polyether polycarbonate 3 | 7.5 |
| Ethanol | q.s. to 100 |

Above composition was applied onto wet hair using a pump spray and hair was easily blow-dried while brushing and set into a style.

EXAMPLE 2

|  | % by weight | |
| --- | --- | --- |
|  | A | B |
| Polyether polycarbonate 4 | 5.0 | — |
| Luviset CAN | 5.0 | 10.0 |
| Ethanol | q.s. to 100 | |

Above composition was filled into an aerosol can as follows:

|  | % by weight |
| --- | --- |
| Bulk | 50 |
| LPG | 50 |

Aerosol sprays was applied onto a wet hair which was shampooed and towel dried. It was observed that hair treated with the inventive composition was easily blow-dried while brushing and set into a style, whereas the hair treated with comparative composition not comprising Polyether polycarbonate 4 was not easily blow-dried while brushing and set into a style.

Similar results were observed with the following examples.

EXAMPLE 3

|  | % by weight |
| --- | --- |
| Polyether polycarbonate 1 | 4.0 |
| Omnirez 2000 | 2.0 |
| Plascize L2700 | 1.0 |
| Ethanol | q.s. to 100 |

Above composition was filled into an aerosol can as follows:

|  | % by weight |
| --- | --- |
| Bulk | 50 |
| DME | 50 |

EXAMPLE 4

|  | % by weight | |
| --- | --- | --- |
|  | A | B |
| Polyether polycarbonate 4 | 3.5 | — |
| Omnirez 2000 | 3.5 | 3.5 |
| Luviset CAN | 0.68 | 0.68 |
| Plascize L2700 | 0.4 | — |
| DC 200 5CST | 0.1 | 0.1 |
| Fragrance | 0.1 | 0.1 |
| Ethanol | q.s. to 100 | |

Above composition was filled into an aerosol can as follows:

|  | % by weight |
| --- | --- |
| Bulk | 53 |
| Propane/Butane 2.7 bar | 10 |
| DME | 37 |

Aerosol spray was applied onto a wet hair which was shampooed and towel dried. It was observed that hair treated with the inventive composition was easily blow-dried while brushing and set into a style, whereas the hair treated with comparative composition not comprising Polyether polycarbonate 4 was not easily blow-dried while brushing and set into a style.

EXAMPLE 5

|  | % by weight |
| --- | --- |
| Polyether polycarbonate 3 | 3.0 |
| Omnirez 2000 | 3.5 |
| Plascize L2700 | 0.35 |
| DC556 Cosmetic Grade Fluid | 0.1 |
| Uvinul MC80N | 0.05 |
| Ethanol | q.s. to 100 |

Above composition was filled into an aerosol can as follows:

|  | % by weight |
| --- | --- |
| Bulk | 51 |
| Propane/Butane 4.2 bar | 12 |
| DME | 37 |

Aerosol spray was applied onto wet hair for easy blow drying and on dry hair for creative finger styling.

EXAMPLE 6

|  | % by weight |
| --- | --- |
| Polyether polycarbonate 4 | 2.5 |
| Omnirez 2000 | 5 |
| DC 200 Fluid 1CST | |
| Fragrance | 0.1 |
| Ethanol | q.s. to 100 |

Above composition was filled into an aerosol can as follows:

|  | % by weight |
| --- | --- |
| Bulk | 50 |
| DME | 50 |

Aerosol spray was applied onto wet hair for easy blow drying and on dry hair for creative finger styling.

EXAMPLE 7

|  | % by weight |
| --- | --- |
| Polyether polycarbonate 1 | 2.25 |
| Luviset CAN | 2.75 |
| Fragrance | 0.1 |
| Uvinul MC81N | 0.1 |
| Ethanol | q.s. to 100 |

Above composition was filled into an aerosol can as follows:

|  | % by weight |
| --- | --- |
| Bulk | 50 |
| DME | 50 |

Aerosol spray was applied onto dry hair for bodyfying and volumizing.

EXAMPLE 8

|  | % by weight |
| --- | --- |
| Polyether polycarbonate 1 | 2.0 |
| Omnirez 2000 | 6.0 |
| Fragrance | 0.1 |
| Wheat Protein | 0.1 |
| Ethanol | q.s. to 100 |

Above composition was filled into an aerosol can as follows:

|  | % by weight |
| --- | --- |
| Bulk | 50 |
| DME | 50 |

Aerosol spray was applied onto dry hair for flexible fixing.

EXAMPLE 9

|  | % by weight |
| --- | --- |
| Polyether polycarbonate 1 | 3.5 |
| Omnirez 2000 | 4.7 |
| Plascize L2700 | 0.2 |
| Fragrance | 0.1 |
| Wheat Protein | 0.1 |
| Ethanol | q.s. to 100 |

Above composition was filled into an aerosol can as follows:

|  | % by weight |
| --- | --- |
| Bulk | 50 |
| Propane/Butane 2.7 bar | 10 |
| DME | 40 |

Aerosol spray was applied onto wet hair for easy blow drying and also to reduce frizz.

EXAMPLE 10

|  | % by weight |
| --- | --- |
| Polyether polycarbonate 1 | 2.5 |
| Gantrez ES 225 | 5.0 |
| Fragrance | 0.1 |
| Uvinul MC 80N | 0.1 |
| Ethanol | q.s. to 100 |

Above composition was filled into an aerosol can as follows:

|  | % by weight |
| --- | --- |
| Bulk | 50 |
| DME | 50 |

Aerosol spray was applied onto dry hair for flexible fixing.

EXAMPLE 11

|  | % by weight |
| --- | --- |
| Polyether polycarbonate 1 | 2.5 |
| Gantrez ES 425 | 5.0 |
| Omnirez 2000 | 5.0 |
| Plascize L2700 | 0.3 |
| DC 200 Fluid 1CST | 0.1 |
| Fragrance | 0.1 |

-continued

| | % by weight |
|---|---|
| Uvinul MC 80N | 0.1 |
| Ethanol | q.s. to 100 |

Above composition was filled into an aerosol can as follows:

| | % by weight |
|---|---|
| Bulk | 50 |
| DME | 50 |

Aerosol spray was applied onto wet hair for easy blow drying and shaping and on dry hair for flexible fixing.

The invention claimed is:

1. A method of setting a hair style, the method comprising setting (i) wet hair or (ii) wet hair that was washed with a cleansing composition and towel dried immediately before application of a substantially anhydrous composition into a hair style after applying the substantially anhydrous composition thereon, wherein the substantially anhydrous composition comprises one or more polymers according to the general structure

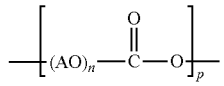

wherein A is a $C_2$ to $C_6$ alkylene group and n represents an average number of 5 to 1000 and p represents an average number of 5 to 100, wherein water content of the substantially anhydrous composition is less than 5% by weight, calculated to the total composition excluding propellant, wherein the substantially anhydrous composition comprises an organic solvent, selected from the group consisting of ethanol, propanol, isopropanol, acetone, n-pentane, isopentane and mixtures thereof, at a concentration in the range of 70 to 99.9% by weight, calculated to the total composition excluding propellant wherein application of the substantially anhydrous composition onto the hair comprises spraying the substantially anhydrous composition onto the hair before setting the hair into the hair style.

2. The method according to claim 1 further comprising blow-drying the hair while brushing the hair and setting the hair into the hair style after application of the substantially anhydrous composition.

3. The method according to claim 1 wherein the one or more polymers have an average molecular weight in the range of 50,000 to 1,000,000.

4. The method according to claim 1 wherein the one or more polymers comprise at least two alkyleneoxy groups.

5. The method according to claim 1 wherein the substantially anhydrous composition comprises the one or more polymers at a concentration in the range of 0.1 to 30% by weight calculated to the total composition excluding propellant.

6. The method according to claim 5 wherein the substantially anhydrous composition comprises an anionic polymer at a concentration in the range of 0.5 to 20% by weight calculated to the total composition excluding propellant.

7. The method according to claim 1, wherein the substantially anhydrous composition comprises ethanol.

8. The method according to claim 6 wherein the weight ratio of the one or more polymers to the anionic polymer is in the range of 2:8 to 8:2.

9. The method according to claim 1 wherein the substantially anhydrous composition comprises at least one oil at a concentration in the range of 0.01 to 10% by weight calculated to the total composition excluding propellant.

10. The method according to claim 1 wherein the substantially anhydrous composition is an aerosol composition and comprises at least one propellant at a concentration in the range of 1 to 95% by weight calculated to the total of aerosol composition.

11. The method according to claim 4 wherein the one or more polymers comprise a combination of an ethyleneoxy group and a propyleneoxy group.

12. The method according to claim 5 wherein the substantially anhydrous composition comprises the one or more polymers at a concentration in the range of 2 to 10% by weight calculated to the total composition excluding propellant.

* * * * *